United States Patent
Wulfman

[11] Patent Number: 5,843,103
[45] Date of Patent: Dec. 1, 1998

[54] SHAPED WIRE ROTATIONAL ATHERECTOMY DEVICE

[75] Inventor: Edward I. Wulfman, Woodinville, Wash.

[73] Assignee: SciMed Life Systems, Inc., Maple Grove, Minn.

[21] Appl. No.: 812,568

[22] Filed: Mar. 6, 1997

[51] Int. Cl.$^6$ .................................................. A61B 17/22
[52] U.S. Cl. ........................... 606/159; 606/170; 606/180
[58] Field of Search .................................. 606/159, 180, 606/170

[56] References Cited

U.S. PATENT DOCUMENTS

| | | | |
|---|---|---|---|
| 4,883,460 | 11/1989 | Zanetti | 604/22 |
| 5,314,438 | 5/1994 | Shturman | 606/180 |
| 5,360,432 | 11/1994 | Shturman | 606/159 |
| 5,584,843 | 12/1996 | Wulfman et al. | 606/159 |

*Primary Examiner*—Michael Buiz
*Assistant Examiner*—Julian W. Woo
*Attorney, Agent, or Firm*—Westman, Champlin & Kelly, P.A.

[57] ABSTRACT

An atherectomy device is used for removing a restriction in a blood vessel. The atherectomy device includes a cutting portion having a lumen therein, the lumen being sized to track over a guidewire, wherein an outer surface of the cutting portion comprises a cutting surface. An elongate shaping member is cooperable with the cutting portion and is disposed generally longitudinally relative to the cutting portion. The shaping member has an insertion conformation and an expanded conformation. The expanded conformation is radially expanded relative to the insertion conformation. The shaping member is configured to deform the cutting portion from an insertion shape into a cutting shape as the shaping member moves from the insertion conformation to the expanded conformation. A drive shaft is coupled to a proximal end of the cutting portion and is configured to be rotationally driven.

30 Claims, 7 Drawing Sheets

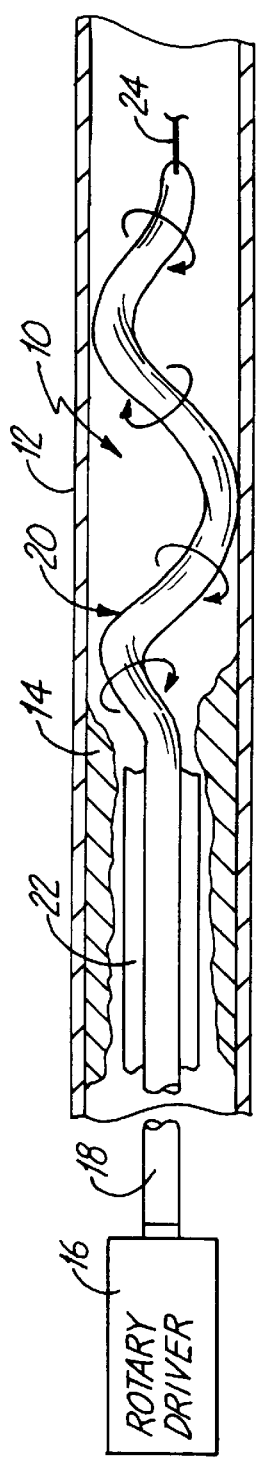
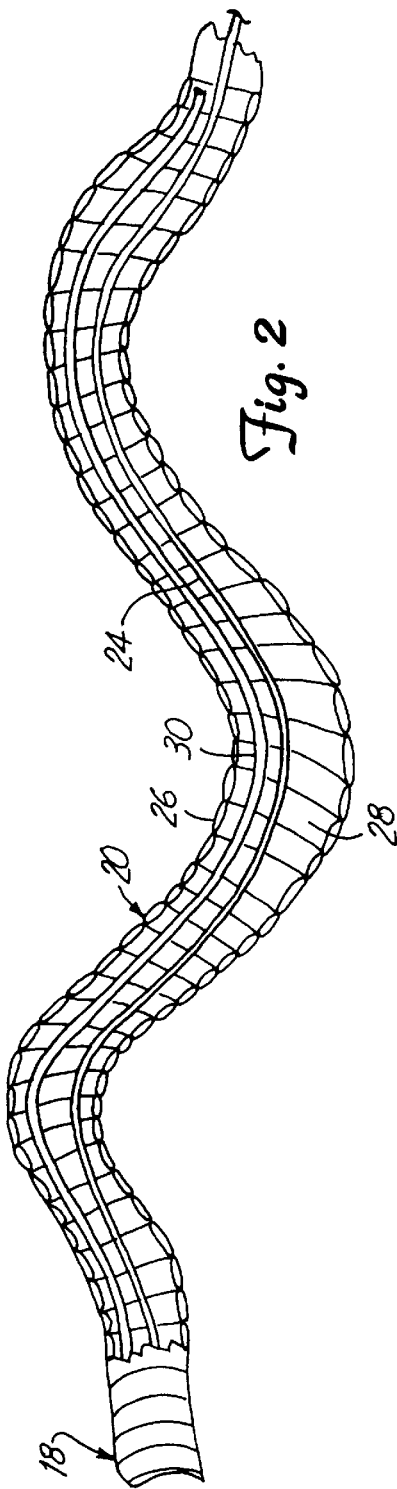
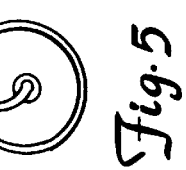

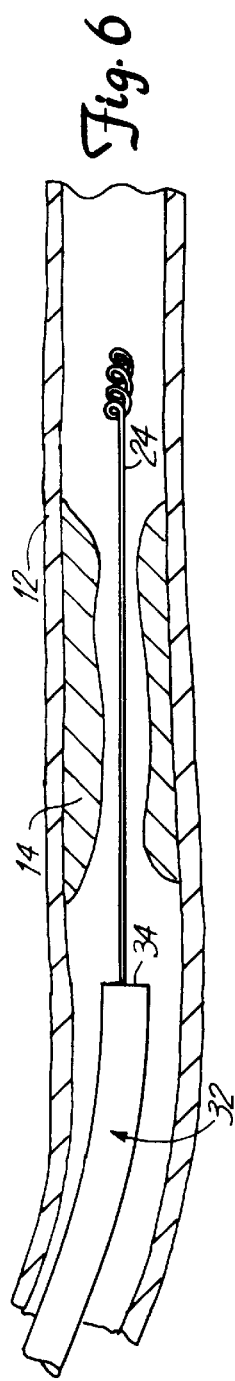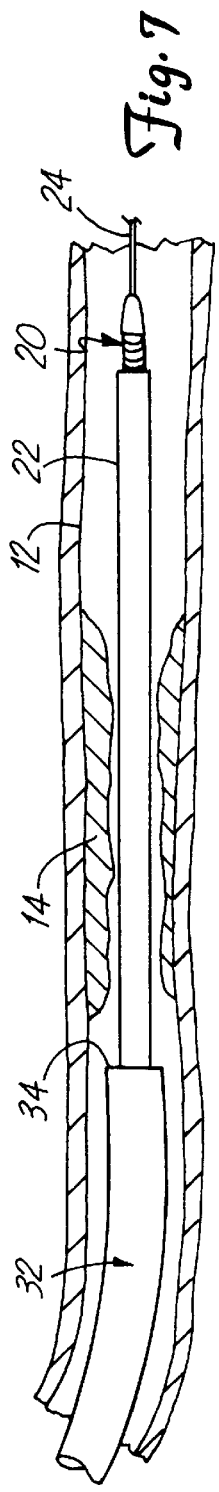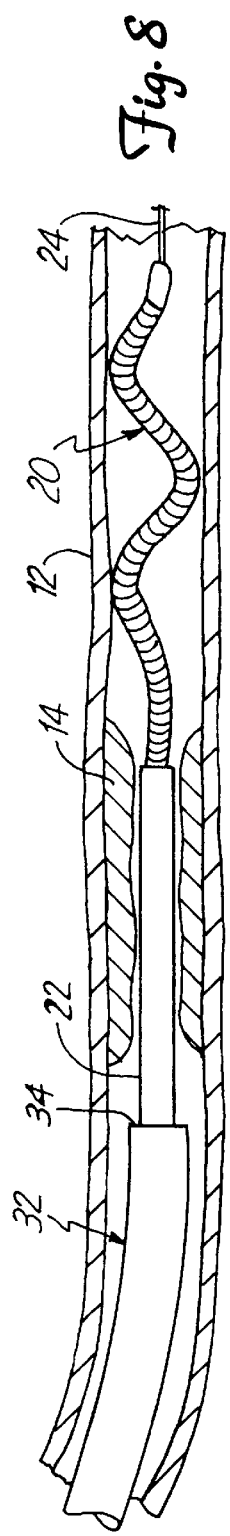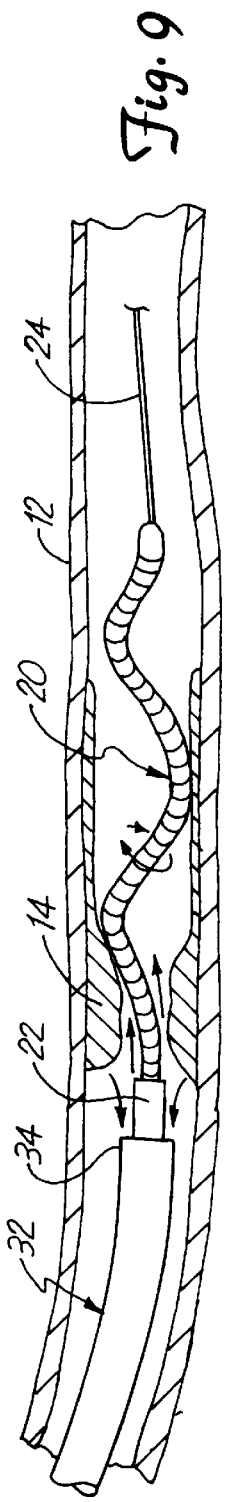

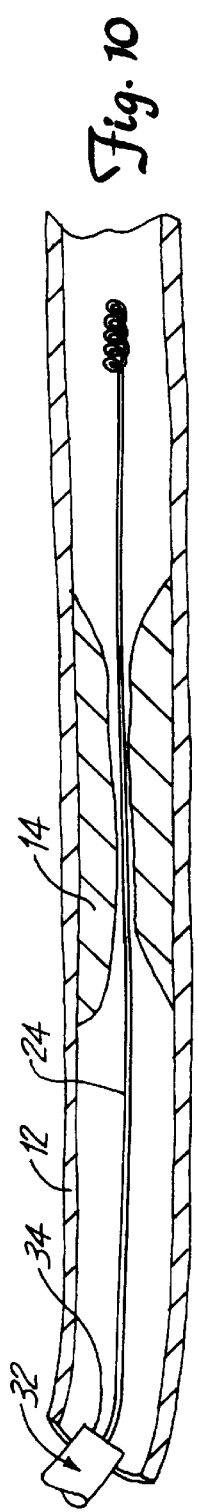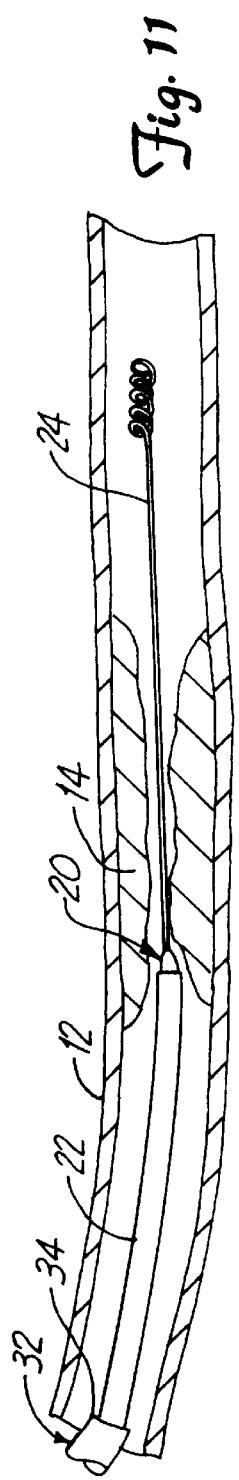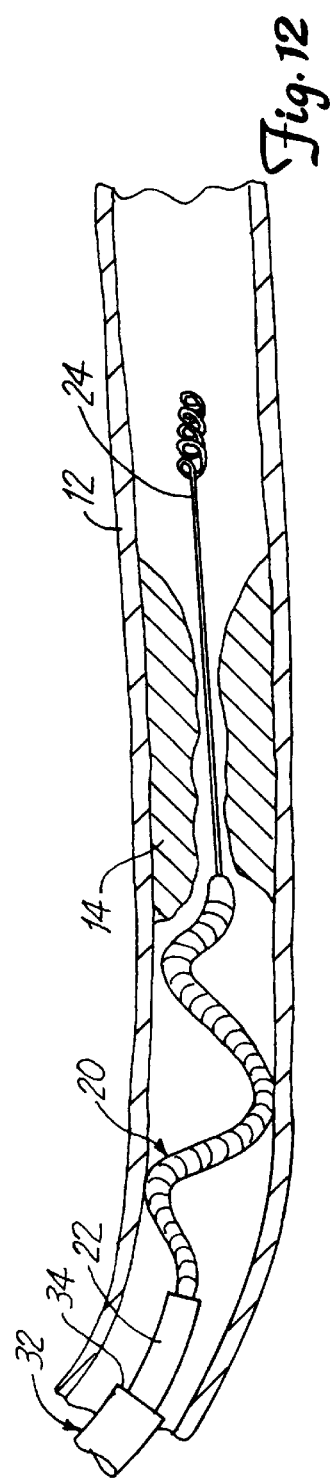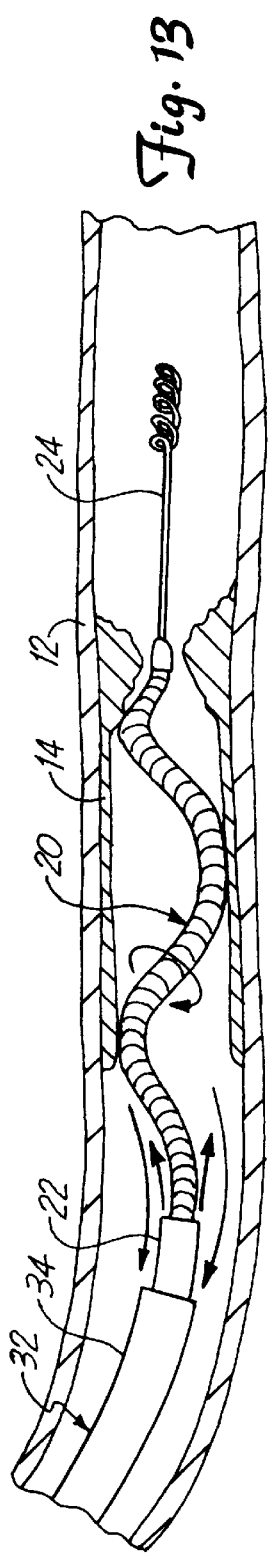

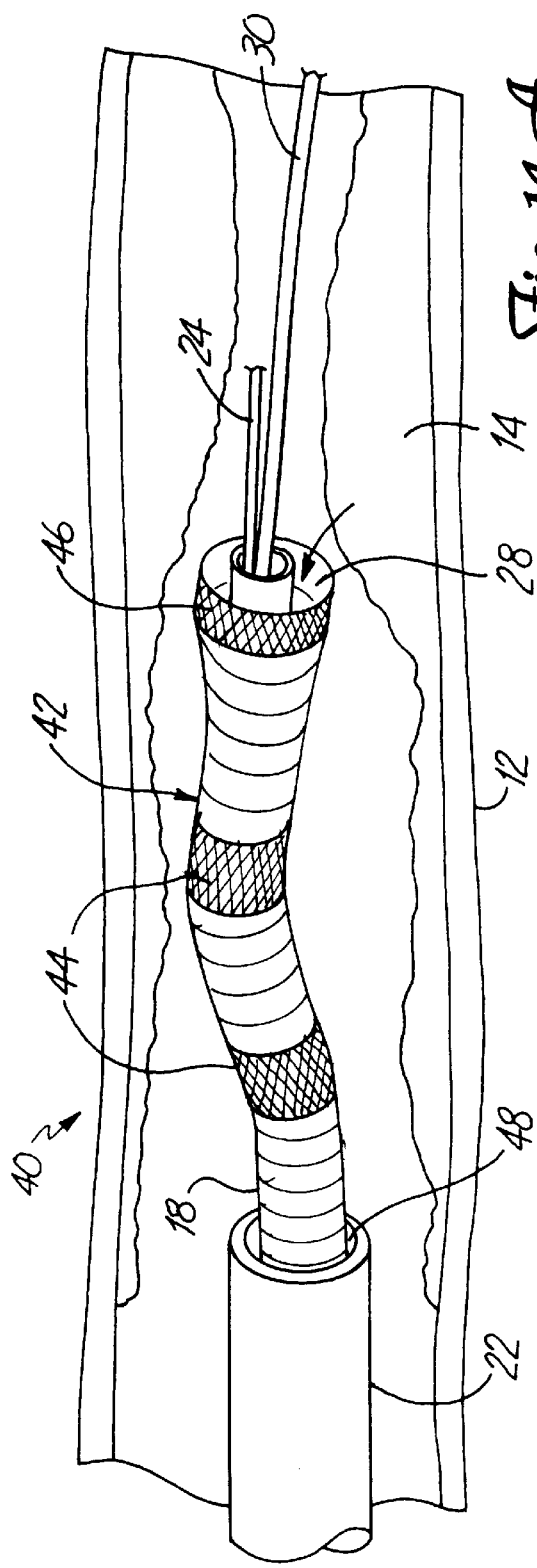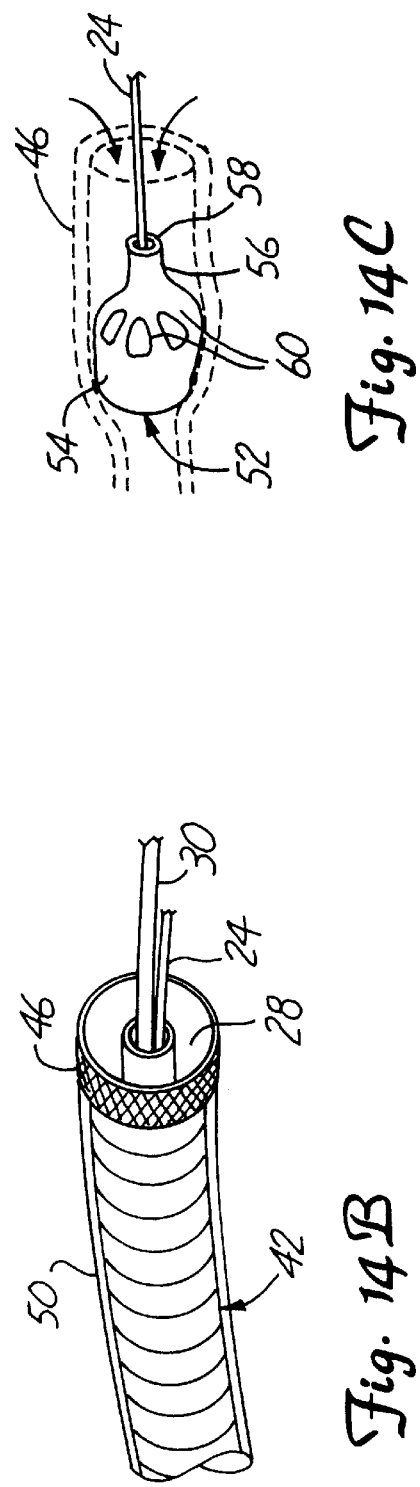

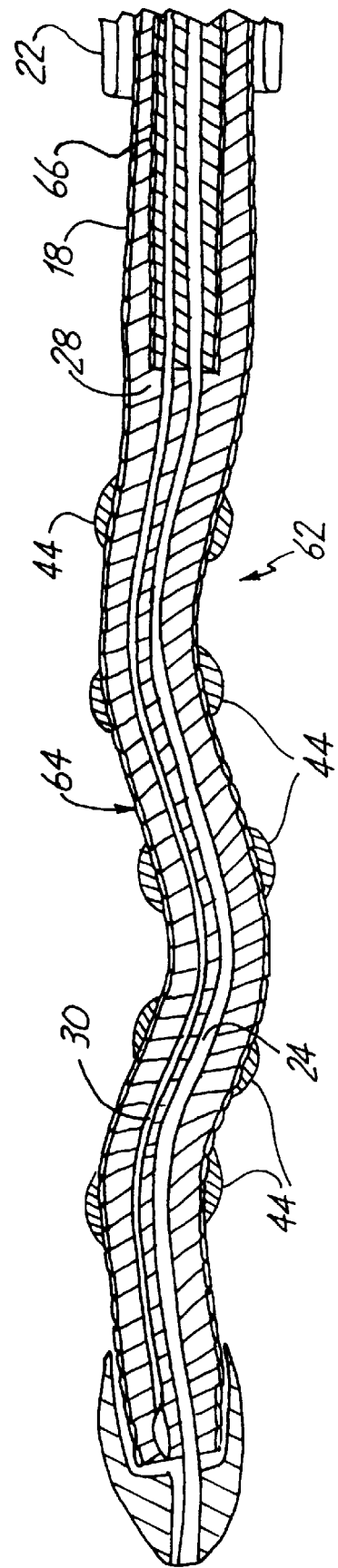

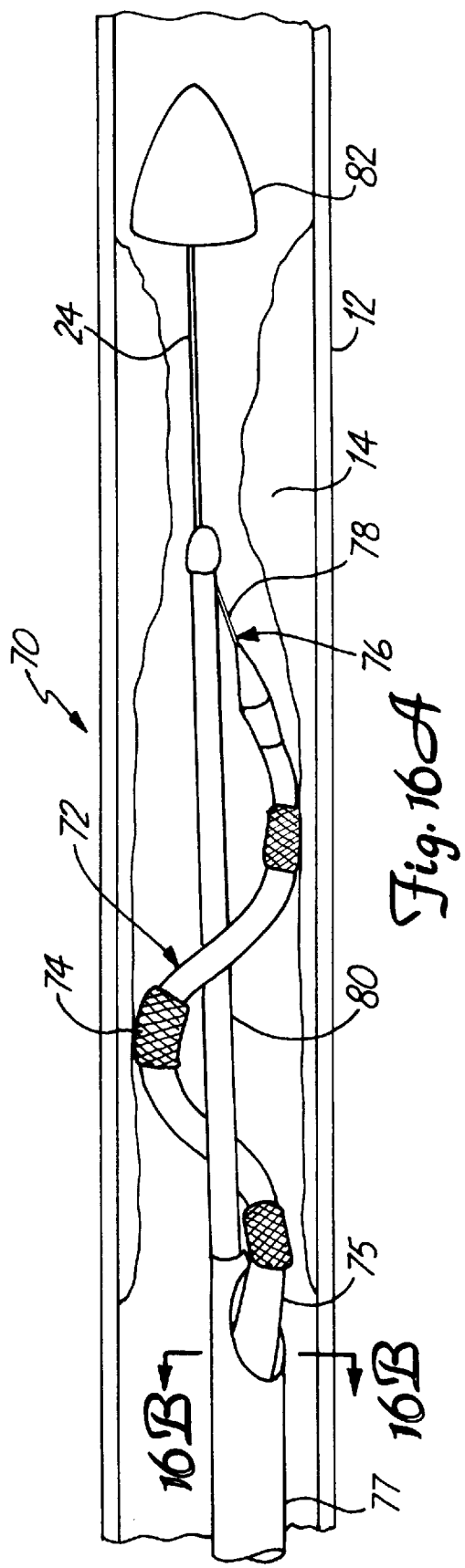
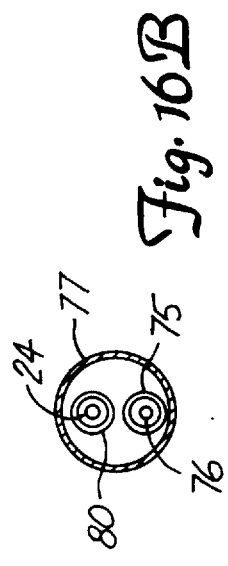
Fig. 16A
Fig. 16B

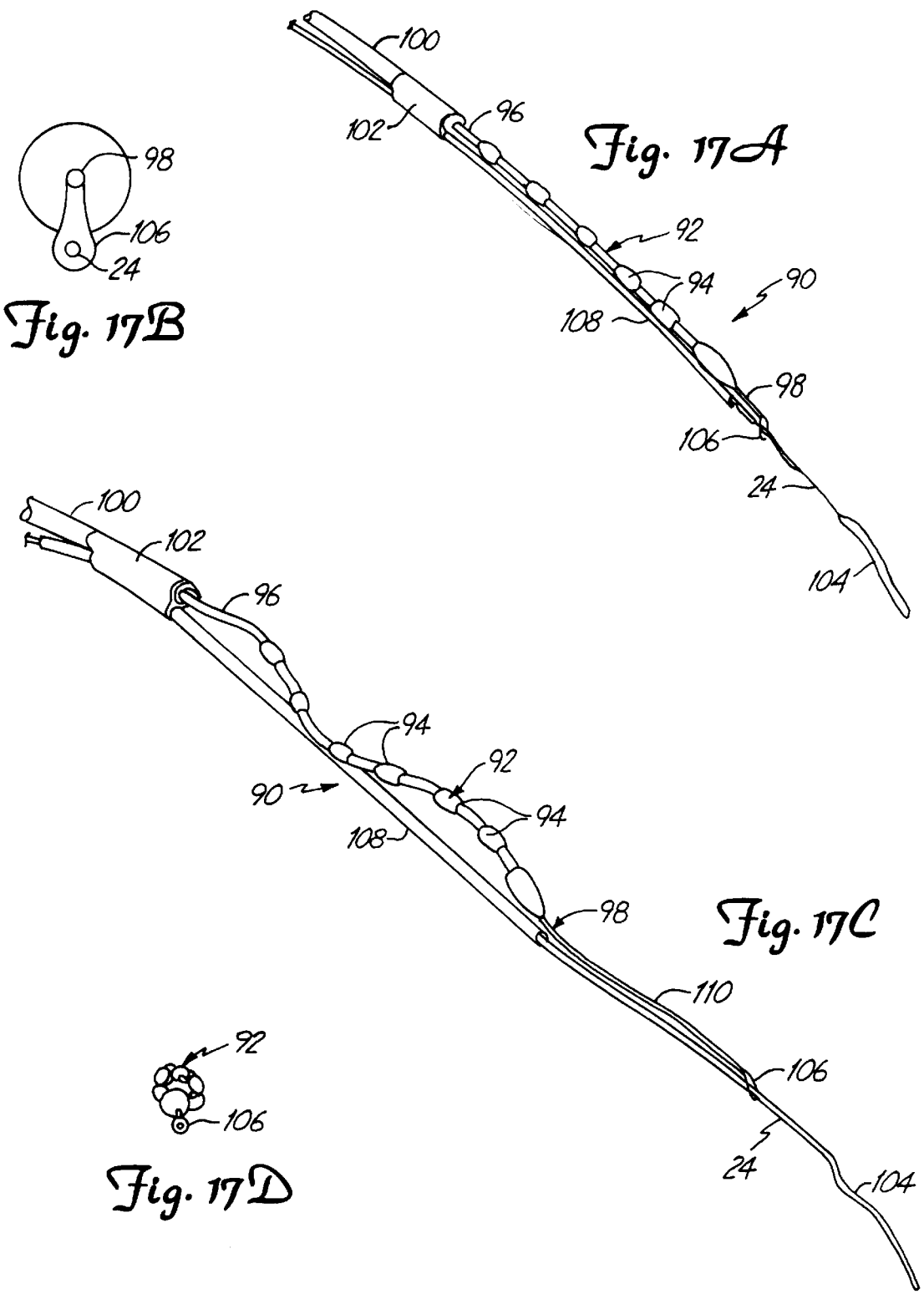

ововhat# SHAPED WIRE ROTATIONAL ATHERECTOMY DEVICE

INCORPORATION BY REFERENCE

The following U.S. Patent is hereby fully incorporated by reference the Wulfman et al. U.S. Pat. No. 5,584,843 entitled SHAPED WIRE MULTI-BURR ROTATIONAL ABLATION DEVICE, which issued on Dec. 17, 1996 and which is assigned to the same assignee as the present application.

The following co-pending U.S. patent application Ser. Nos. 08/813,794 and 08/810,825, both of which are entitled DISTAL PROTECTION DEVICE, were filed on even date herewith, and are assigned to the same assignee as the present application, and both of which are hereby incorporated by reference.

BACKGROUND OF THE INVENTION

The present invention relates to an atherectomy device. More specifically, the present invention relates to a shaped-wire, rotational atherectomy device for removing a restriction from a body vessel.

Blood vessels can become occluded (blocked) or stenotic (narrowed) in one of a number of ways. For instance, a stenosis may be formed by an atheroma which is typically a harder, calcified substance which forms on the lumen walls of the blood vessel. Also, the stenosis can be formed of a thrombus material which is typically much softer than an atheroma, but can nonetheless cause restricted blood flow in the lumen of the blood vessel. Thrombus formation can be particularly problematic in a saphenous vein graft (SVG).

Two different procedures have developed to treat a stenotic lesion (stenosis) in vasculature. The first is to deform the stenosis to reduce the restriction within the lumen of the blood vessel. This type of deformation (or dilatation) is typically performed using balloon angioplasty.

Another method of treating stenotic vasculature is to attempt to completely remove either the entire stenosis, or enough of the stenosis to relieve the restriction in the blood vessel. Removal of the stenotic lesion has been done through the use of radiofrequency (RF) signals transmitted via conductors, and through the use of lasers, both of which treatments are meant to ablate (i.e., superheat and vaporize) the stenosis. Removal of the stenosis has also been accomplished using thrombectomy or atherectomy. During thrombectomy and atherectomy, the stenosis is mechanically cut or abraded away from the vessel.

One device which has been developed for abrading a stenosis, and which represents a significant advancement in the art, is set out in the above incorporated U.S. Pat. No. 5,584,843 (the Wulfman et al. patent). Wulfman et al. teach a rotatable drive shaft which is advanceable over a shaped wire. The rotatable drive shaft includes cuffs which extend radially off of the outer surface of the drive shaft, and which are covered with a cutting material, such as diamond grit. The drive shaft, when advanced over the shaped wire, assumes a gentle S, helical or corkscrew shape thus providing an overall conformation which is radially larger than the overall conformation of the drive shaft in a simply linear, or unshaped, configuration.

The device set out in Wulfman et al. requires that either the guidewire be preformed into the gentle S, helical or corkscrew shape or the guidewire have a substantially linear configuration and that a hypotube, which is advanceable over the guidewire, is preformed into an S, helical or corkscrew shape. In the latter embodiment, after the hypotube is advanced over the guidewire, the drive shaft must be advanced over the hypotube. In either case, once the drive shaft is advanced over the preshaped member, the drive shaft assumes the larger conformation defined by the preshaped member. The drive shaft is then rotated such that the cuffs which contain the cutting surfaces for the device engage and abrade the stenosis.

SUMMARY OF THE INVENTION

The present invention is directed to a rotational atherectomy device which provides advantages over devices found in the prior art. For example, in one embodiment of the present invention, the atherectomy device accommodates a standard guidewire or other guidewire type device, such as a wire with a 0.014 inch outer diameter or other such device. In another embodiment, distal aspiration of emboli is provided which enhances the atherectomy procedure.

An atherectomy device is used for removing a restriction in a blood vessel. The atherectomy device includes a cutting portion having a lumen therein, the lumen being sized to accommodate a guidewire, wherein an outer surface of the cutting portion comprises a cutting surface. An elongate shaping member is cooperable with the cutting portion and is disposed generally longitudinally relative to the cutting portion. The shaping member has an insertion conformation and an expanded conformation. The expanded conformation is radially expanded relative to the insertion conformation. The shaping member is configured to deform the cutting portion from an insertion shape into a cutting shape as the shaping member moves from the insertion conformation to the expanded conformation. A drive shaft is coupled to a proximal end of the cutting portion and is configured to be rotationally driven.

BRIEF DESCRIPTION OF THE DRAWINGS

FIG. 1 is a cross-sectional, pictorial view of one embodiment of the present invention.

FIG. 2 is a greatly enlarged view of a cutting portion of the present invention illustrated in FIG. 1.

FIG. 3 is a transverse cross-sectional view illustrating the placement of a shaping member, and a guidewire, within the cutting portion of the atherectomy device of the present invention.

FIGS. 4 and 5 illustrate two preferred shapes of the shaping member in accordance with the present invention.

FIGS. 6–9 illustrate the use of an atherectomy device in accordance with one aspect of the present invention.

FIGS. 10–13 illustrate the use of an atherectomy device in accordance with another aspect of the present invention.

FIGS. 14A–14C illustrate an atherectomy device in accordance with another feature of the present invention in which the atherectomy device is provided with an aspiration lumen and configuration.

FIG. 15 illustrates an atherectomy device in accordance with another feature of the present invention in which an inner protection member is provided.

FIGS. 16A and 16B illustrate an atherectomy device wherein the guide wire has a protective sheath in accordance with another aspect of the present invention.

FIGS. 17A–17D illustrate an atherectomy device which is not coaxial with a guidewire, and wherein the guidewire has a protective sheath in accordance with another aspect of the preset invention.

DETAILED DESCRIPTION OF THE PREFERRED EMBODIMENTS

FIG. 1 illustrates atherectomy device 10 deployed in a vessel 12 which includes stenosis 14. In the embodiment shown in FIG. 1, device 10 includes a rotary driver 16 which is coupled to a rotatable drive shaft 18. Drive shaft 18 includes a cutting portion 20 at a distal end thereof. Cutting portion 20 is either a separate cutting portion which is attached to the distal end of drive shaft 18, or is a portion of drive shaft 18 which is simply formed as cutting portion 20. Device 10 also includes, in the embodiment shown in FIG. 1, insertion sheath 22, which is advanced over drive shaft 18 and cutting portion 20 during insertion of device 10 into the lumen of vessel 12. FIG. 1 further illustrates that, in the preferred embodiment, device 10 is advanced over a guidewire 24 for proper placement within the lumen of vessel 12.

As will be described in greater detail later in the specification, device 10 is preferably introduced into the lumen of vessel 12 with sheath 22 advanced over cutting portion 20 of device 10. This causes cutting portion 20 to assume an insertion conformation which is substantially linear. Sheath 22 is then withdrawn from cutting portion 20, thus releasing cutting portion 20 to assume a pre-formed, radially expanded cutting conformation. The operator then actuates rotary driver 16 such that drive shaft 18 causes cutting portion 20 to rotate about the longitudinal axis of drive shaft 18 and cutting portion 20. In the preferred embodiment, the outer surface of cutting portion 20 includes a cutting mechanism or abrasive material, such as a blade, or diamond grit. Therefore, when cutting portion 20 is rotating, it is moved through the lumen of vessel 12, across stenosis 14 and thus cuts away stenosis 14 to debulk the lumen of vessel 12 in the area of stenosis 14.

In a preferred embodiment, the cutting operation performed by device 10 leaves behind only microscopic particles of stenosis 14 (on the order of 5 microns or less). However, it should be noted that a suitable distal protection device can also be used in combination with cutting device 10 in order to protect distal flow from the stenotic debris which is separated from stenosis 14 during the cutting procedure. Two such suitable distal protection devices are set out in copending U.S. patent application Ser. Nos. 08/813,794 and 08/810,825, both of which are entitled DISTAL PROTECTION DEVICE, were filed on Mar. 6, 1997, and are assigned to the same assignee as the present application, and both of which are hereby incorporated by reference.

Briefly, the devices set out in the incorporated patent applications are devices which are inserted, distal of stenosis 14, and then deployed to collect stenotic debris which flows distally of stenosis 14 after the cutting procedure. The debris is then removed, along with the distal protection device, when the procedure is finished.

The Wulfman et al. patent incorporated herein by reference discloses a preferred system for attaching drive shaft 18 to rotary driver 16. Briefly, a sealed chamber having an injection port is provided about a region of drive shaft 18 which is coupled to the output of rotary driver 16. A sheath communicates with the interior of the sealed chamber and extends distally about drive shaft 18. The injection port is provided so that drugs or fluids can be injected into the lumen of the sheath surrounding drive shaft 18. In that preferred embodiment, flexible drive shaft 18 is passivated with a coating of low-friction material, such as Dupont's TEFLON® brand of polytetraflouroethylene (PTFE).

Rotary driver 16 is preferably a variable speed rotary driver, which speed can be varied by the operator. Rotary driver 16 can also optionally be a fixed speed rotary driver, the actuation of which is controlled by the operator. In either case, rotary driver 16 is preferably suitable for rotating flexible drive shaft 18 at a speed in a range of from approximately 10,000 rpm to greater than 160,000 rpm, and preferably as high as between 190,000 rpm to 225,000 rpm.

Also, as disclosed in the Wulfman et al. patent, guidewire 24 can be coupled to a low speed rotary driver so that it can be driven at low speeds as well.

FIG. 2 is a greatly enlarged cross-sectional view of cutting portion 20 which is preferably between about 1 cm and 10 cm in length. FIG. 2 illustrates that cutting portion 20 preferably includes an outer tube 26 which defines a lumen 28 therein. FIG. 2 also illustrates that cutting portion 20 preferably includes shaping member 30 which either extends through lumen 28, or ends proximal of the distal end of cutting portion 20. Further, as shown in FIG. 2, guidewire 24 extends through lumen 28.

In the preferred embodiment, both flexible drive shaft 18, and the outer tube 26 of cutting portion 20 are formed of a multi-filar helical wound drive shaft with an inner diameter of approximately 0.024 inches and an outer diameter of approximately 0.035 inches. Further, in one preferred embodiment, the multi-filar helical winding is a tri-filar helical winding. Of course, the sizes and configuration of drive shaft 18 and cutting portion 20 will vary with application.

Also, in the preferred embodiment, guidewire 24 is preferably a standard steel guidewire or hypotube having an outer diameter of approximately 0.014 inches. However, any other standard guidewire can also be used.

Further, in the preferred embodiment, shaping member 30 is preferably any suitable preformable material such as stainless steel, a heat settable polymer material, or other suitable shape memory material having an outer diameter of approximately 0.007 inches.

FIG. 3 is a transverse cross-sectional view of cutting portion 20. FIG. 3 illustrates an embodiment in which shaping member 30 resides within lumen 28 of cutting portion 20. In the embodiment shown in FIG. 3, cutting portion 20 is rotatably driven by drive shaft 18 and is rotatable about both guidewire 24 and shaping member 30.

Shaping member 30 is preferably preformed into either a gentle S shape, or into a helical, corkscrew, or other suitable, radially expanded shape. FIG. 4 illustrates an end view of shaping member 30 formed into a gentle S shape, while FIG. 5 illustrates an end view of shaping member 30 formed into a corkscrew or helical shape. In any case, shaping member 30 and outer tube 26 of cutting portion 20 are preferably flexible such that cutting portion 20 can reside in a restrained, insertion position in which cutting portion 20 has a substantially linear overall conformation. Then, when released, shaping member 30 drives cutting portion 20 into the cutting shape illustrated in FIGS. 1 and 2 in which the cutting portion has a radially expanded overall conformation relative to that in the insertion position.

In one preferred embodiment, cutting portion 20 is formed as shown in FIG. 2, except with two complete wavelengths in the overall conformation of cutting portion 20, wherein the amplitude of the waves in shaping member 30 is approximately 0.125 inches and the wavelength is approximately 1.0 inches.

FIGS. 6–9 illustrate the use of atherectomy device 10 in accordance with one aspect of the present invention. In a preferred embodiment, a distal protection device (not shown) is first inserted across stenosis 14 and deployed distally of stenosis 14. Standard guidewire 24 and guide catheter 32 are advanced through the lumen of vessel 12 to a region proximate stenosis 14. Guidewire 24 is advanced across stenosis 14.

FIG. 7 illustrates that once guidewire 24 and guide catheter 32 are appropriately positioned, atherectomy device 10 is advanced over guidewire 24, with sheath 22 substantially covering cutting portion 20 of atherectomy device 10. Sheath 22 is preferably formed of a suitable polymer material, such that it can be advanced over drive shaft 18 and cutting portion 20 of atherectomy device 10. With sheath 22 covering atherectomy device 10 as shown in FIG. 7, atherectomy device 10 is retained in its insertion position, which is substantially linear and radially collapsed. At least cutting portion 20 of atherectomy device 10 is then advanced across stenosis 14 such that it resides distally of stenosis 14.

FIG. 8 illustrates that, once atherectomy device 10 is positioned as shown in FIG. 7, sheath 22 is withdrawn from cutting portion 20 to allow shaping member 30 to drive cutting portion 20 from its insertion position (shown in FIG. 7) to the cutting position shown in FIG. 8. As discussed previously, the cutting position has an overall conformation which is radially expanded relative to that of the insertion position. This allows cutting portion 20 to debulk a portion of the lumen of vessel 12 which has a larger diameter than simply the outer diameter of tube 26 forming the outer surface of cutting portion 20.

Then, as shown in FIG. 9, the operator actuates rotary driver 16 to cause rotation of drive shaft 18 and cutting portion 20 and withdraws drive shaft 18, and consequently cutting portion 20, proximally within the lumen of vessel 12 across stenosis 14. This causes cutting portion 20 to abrade, or cut away, a portion of stenosis 14 thus enlarging the lumen of vessel 12 through stenosis 14. Also, as illustrated in FIG. 9, infusate can be optionally injected through sheath 22 or guide catheter 32. Such infusate may include, for example, any suitable pharmacological agent for treating stenosis 14, or simply a wash solution which can be used to wash the fragments of stenotic debris from the lumen of vessel 12. FIG. 9 further illustrates that aspiration of the stenotic debris can optionally be performed through guide catheter 32, or sheath 22.

Once the cutting operation is completed, sheath 22 is again advanced over cutting portion 20 to drive cutting portion 20 to its insertion position. Device 10, catheter 32, guidewire 24 and any distal protection device are then all removed from vessel 12.

FIGS. 10–13 illustrate the use of atherectomy device 10 in accordance with another aspect of the present invention. The use of atherectomy device 10 as shown in FIGS. 10–13 is somewhat similar to that shown in FIGS. 6–9. In accordance with the preferred embodiment, a distal protection device (not shown) is first inserted across stenosis 14 and deployed distally of stenosis 14.

However, instead of advancing cutting portion 20 of atherectomy device 10 across lesion 14 from a distal end thereof, to a proximal end thereof, cutting portion 20 is advanced from a proximal end of stenosis 14 to a distal end thereof. This technique may be used, for example, when the restriction provided by stenosis 14 is more severe, or more diffuse. Rather than being required to advance the entire cutting portion 20 of atherectomy device 10, along with sheath 22, across stenosis 14, only guidewire 24 needs to be advanced across stenosis 14. This is shown in FIG. 10.

In other words, guide catheter 32 is preferably positioned such that its distal end 34 is spaced from, and proximate to, stenosis 14. Guidewire 24 is advanced across stenosis 14, to a distal end thereof. Then, as shown in FIG. 11, atherectomy device 10 is advanced over guidewire 24, in the insertion position, to a region of vessel 12 just proximal of stenosis 14.

As illustrated in FIG. 12, sheath 22 is then withdrawn from at least cutting portion 20 of atherectomy device 10 so that cutting portion 20 forms its cutting shape. Of course, it should be noted that, rather than withdrawing sheath 22 from cutting portion 20, cutting portion 20 can be advanced out from within sheath 22. In either case, cutting portion 20 forms the overall conformation which is radially expanded relative to that of the insertion position shown in FIG. 11.

Next, as shown in FIG. 13, the operator actuates rotary driver 16 causing rotation of drive shaft 18 and cutting portion 20. Cutting portion 20 of device 10 is advanced across stenosis 14 to debulk the lumen of vessel 12 in the area of stenosis 14. Infusion and aspiration can also be implemented, as described with reference to FIG. 9.

Sheath 22 is then again advanced over cutting portion 20 to cause cutting portion 20 to resume its insertion shape. Then, atherectomy device 10, guide catheter 32 and guidewire 24 are all removed from vessel 12, as is any distal protection device which was used. These items can be removed one at a time, or simultaneously. Also, it should be noted that sheath 22 need not be advanced over cutting portion 20 for removal. Instead, cutting portion 20 can simply be retracted to come within guide catheter 32, and the system can then be removed from vessel 12.

FIGS. 14A–14C illustrate an atherectomy device 40 in accordance with another aspect of the present invention. Atherectomy device 40 is similar to atherectomy device 10 in some ways, and similar items are similarly numbered. However, atherectomy device 40 has cutting portion 42 which includes a plurality of cuffs, or burrs, 44. In the preferred embodiment, burrs 44 are coated with diamond grit, or another suitable abrasive material. FIG. 14A shows atherectomy device 40 placed within the lumen of vessel 12, proximal of stenosis 14, and being advanced across stenosis 14 to a distal end thereof. FIGS. 14A and 14B also show shaping member 30 extending out from within lumen 28. Of course, shaping member 30 can also terminate proximal of the expanded cuff 46 as well.

FIG. 14A also illustrates that atherectomy device 40 includes a distal enlarged cuff or burr 46. Further, sheath 22 has a lumen 48 therein which is radially larger than the outer diameter of cutting portion 42. Thus, in the embodiment shown in FIG. 14A, the inner lumen 28 of cutting member 42 terminates at its distal end in expanded burr 46 which is radially expanded relative to the distal end of cutting member 20 shown in FIGS. 1 and 2. Also, sheath 22 terminates at its distal end in an opening which is preferably expanded relative to that shown in FIGS. 6–13. Lumens 48 and 28 are thus preferably used for infusion, and aspiration, respectively. Aspiration thus occurs at the distal tip of atherectomy device 40 rather than proximal of that point as described with reference to, for example, FIGS. 9 and 13. This type of distal aspiration reduces the likelihood that larger stenotic particles severed or abraded from stenosis 14 will cause embolization in vessel 12.

FIGS. 14B and 14C illustrate the distal tip of cutting portion 42 shown in FIG. 14A, in greater detail to illustrate additional features. FIG. 14B illustrates that, in the preferred embodiment, the longitudinal external surface of cutting portion 42 is preferably coated with a layer 50 of polymer material to enhance the vacuum which can be pulled through the interior lumen 28 to increase the effectiveness of aspiration. In the preferred embodiment, layer 50 is preferably a TEFLON® brand PTFE or other suitable polymer material which is heat of shrunk over the multifillar winding which comprises drive shaft 18 and the major area of cutting portion 42 to provide a vacuum seal therealong. Of course, other suitable methods or techniques of providing a vacuum sealed lumen, such as extrusion of a material over the multifillar winding, or other suitable techniques, can be used as well.

FIG. 14C illustrates a cutting head 52 which is preferably placed within the distal tip region of cutting portion 42. In the preferred embodiment, cutting head 52 has an enlarged exterior surface portion 54 which is coupled to the interior lumen 28 of cutting portion 42, and is rotatable with cutting portion 42. Cutting head 52 also preferably includes a narrowed nose region 56 which has a lumen 58 therethrough. Lumen 58 is sized to receive guidewire 24. Thus, the narrowed nose region 56 and lumen 58 serve to center guidewire 24 within the lumen 28 of cutting portion 42.

Also, in the preferred embodiment, cutting head 52 is provided with a plurality of cutting blades 60 which extend between nose region 56 and expanded region 54. In the preferred embodiment, the cutting blades 60 are simply stainless steel, or other suitable struts which extend between nose region 56 and expanded region 54. Since cutting head 52 is rotatable with cutting member 42 about guidewire 24, cutting blades 60 are configured such that they further reduce the size of any embolic particles aspirated through lumen 28. This increases the effectiveness of the aspiration, and substantially reduces the likelihood that lumen 28 will be clogged with embolic material or particles aspirated therethrough. This also facilitates the passage of more embolic material through a smaller proximal lumen 28 within cutting member 42.

FIG. 15 is a cross-sectional view of an atherectomy device 62 having a cutting portion 64 in accordance with the present invention. Cutting portion 64 is similar to cutting portions 20 and 42, and similar items are similarly numbered. However, cutting portion 64 is formed according to another aspect of the present invention. It has been found that, in some embodiments of a rotating ablation or atherectomy device, where both shaping member 30 and guidewire 24 (and possibly a distal protection device) are positioned coaxially within drive shaft 18 and the cutting portion of the drive shaft, high speed rotation of the drive shaft 18 about the interior devices or wires can impart a twisting force on the wires. This can cause the coaxial wires to twist around one another.

Thus, atherectomy device 62 includes protection member 66 which is located radially between the interior, non-rotating wires, and the exterior, rotating drive shaft 18 (and optionally cutting portion 64). In the preferred embodiment, protection member 66 includes a non-rotating coil which substantially prevents drive shaft 18 from contacting the wires running through the lumen 28 thereof through a majority of the length of drive shaft 18, except for the very distal portion which comprises cutting portion 64. Protection device 66 substantially surrounds the remainder of the non-rotating wires running within lumen 28.

In the embodiment shown in FIG. 15, protection device 66 is preferably a non-rotating coil having an outer diameter of approximately 0.032 inches. Of course, protective member 66 could also be another suitable type of tube or sheath which shields the rotating drive shaft 18 from the wires running through the lumen 28. Shaft 22 is preferably a TEFLON® brand PTFE sheath having an outer diameter of approximately 0.070 inches, and rotating drive shaft 18 preferably has an outer diameter of approximately 0.050 inches. As in the previous embodiments, guidewire 24 preferably is a standard guidwire having an outer diameter of 0.014 inches, and is non-rotating. Similarly, shaping member 30 preferably is a non-rotating member having an outer diameter of approximately 0.008 inches.

FIG. 16A illustrates an atherectomy device 70 in accordance with another aspect of the present invention. Similar items are similar to those shown in the previous figures. Atherectomy device 70 includes cutting portion 74 which has a lumen therein which receives shaping member 76. Shaping member 76 is preferably similar to shaping member 30. The cutting portion 72 also includes a plurality of burrs or cuffs 74 which are coated with diamond grit or another suitable abrasive material. Atherectomy device 70 also includes a proximal sheath 77 which has a lumen that receives rotatable drive shaft 75 coupled to cutting portion 74, and also receives guidewire 24 therein. It has been found that, where cutting portion 74 is configured relative to guidewire 24 as shown in FIG. 16A, cutting portion 24 can abrade the outer surface of guidewire 24 during rotation. Thus, atherectomy device 70 provides a protective sheath 80 over a region of the exterior surface of guidewire 24 where it is surrounded by cutting portion 72. The protective sheath 80 is typically formed of stainless steel, nickel, titanium, or another suitable material which has suitable durability for inhibiting damage to guidewire 24 by rotation of cutting portion 72.

FIG. 16A also illustrates that atherectomy device 70 is configured such that the distal end 78 of shaping member 76 extends out from within the lumen of cutting porion 72 and is coupled to the exterior diameter of protective sheath 80. FIG. 16A further illustrates the use of atherectomy device 70 with a distal protection device 82 which is advanced distal of cutting portion 72 and is used to entrap and remove embolic particles abraded from the stenosis.

FIG. 16B illustrates a transverse crosssectional view of atherectomy device 70. FIG. 16B illustrates that sheath 77 has an interior lumen which is sized to receive drive shaft 75 which is coupled for rotational driving of cutting portion 72, and also shaping member 76. In addition, the lumen of sheath 77 is sized to either be connected to, or receive, protective sheath 80, and also to receive guidewire 24 therethrough.

FIGS. 17A–17D illustrate yet another embodiment of an atherectomy device 90 in accordance with the present invention. Atherectomy device 90 includes cutting portion 92 which preferably has a plurality of cuffs or burrs 94 disposed thereon. As with the previously described cuffs or burrs, cuffs or burrs 94 are preferably coated with a diamond grit or other suitable abrasive material. Cutting portion 92 is preferably coupled, at a proximal end thereof, to a rotatable drive shaft 96. Drive shaft 96 and cutting portion 92 are preferably integrally formed within one another, but can comprise two separate members suitably connected to one another.

Drive shaft 96 and cutting portion 92 preferably have an inner lumen sized to receive a non-rotating shaping member 98. In the preferred embodiment, shaping member 98 is preferably a suitable material for shaping cutting portion 92 into a radially expanded conformation.

In the embodiment shown in FIG. 17A, atherectomy device 90 also includes a proximal sheath 100 which has a cuff 102 disposed thereabout. Sheath 100 is suitable for receiving drive shaft 96 and cutting portion 92 therethrough, and cuff 102 is suitable for providing a mechanism by which sheath 100 tracks over standard guidewire 24. Standard guidewire 24 is provided, at its distal end, with a distal protection device 104 which can be any suitable distal protection device. Also, shaping member 98 is provided, at its distal tip 106, with a loop, or another suitable configuration for being cooperably coupled to guidewire 24. As with the embodiment shown in FIGS. 16A and 16B, guidewire 24 preferably has a protection sheath 108 disposed about a portion thereof in the region of cutting member 92. Sheath 108 serves to protect the exterior surface of guidewire 24 from abrasion resulting from the rotation of cutting member 92.

FIG. 17B is an end view of a portion of atherectomy device 90. FIG. 17B illustrates that the distal end 106 of shaping member 98 is preferably includes a simple loop, or an aperture, for cooperating with guidewire 24.

FIG. 17C illustrates atherectomy device 90 in the deployed, radially expanded position. In the embodiment shown in FIG. 17C, shaping member 98 is preferably shaped into the radially expanded conformation in a region just proximal of the distal end thereof. Therefore, when inserted, the distal end 106 of shaping member 98 is brought into close proximity with the distal end of cutting portion 92. This causes cutting portion 92 to reside over a substantially linear portion 110 of shaping member 98. This, in turn, causes cutting portion 92 to assume a radially collapsed, or linear, conformation shown in FIG. 17A.

However, when cutting portion 92 is to be expanded into the cutting position, shaping member 98 is advanced distally relative to the distal end of cutting portion 92. This causes a shaped region of shaping member 98 to move out from within sheath 100 and cuff 102 and to track within cutting portion 92 causing cutting portion 92 to assume the radially expanded cutting position shown in FIG. 17C. However, protective sheath 108 is preferably longitudinally attached to cuff 102 so that sheath 108 remains over guidewire 24 in the region proximate cutting portion 92. As in the embodiment shown in FIGS. 26A and 16B, sheath 108 is preferably formed of stainless steel, nickel, titanium, or another suitable material which tends to inhibit abrasive damage to guidewire 24.

FIG. 17D is an end view of atherectomy device 90 with cutting portion 92 shown in the expanded portion. In the preferred embodiment, when in the collapsed insertion position, the outer radial diameter of cutting portion 92 is approximately 1.5 mm, and in the expanded position shown in FIG. 17C, the outer radial diameter of the overall conformation formed by cutting portion 90 is preferably 5–6 mm.

It should be noted that cutting portion 92 can be placed within a vessel independently of guidewire 24 and distal protection device 104. In that instance, the distal end 106 of shaping member 98 does not need to be attached to guidewire 24. Rather, the distal protection device 104 and guidewire 24 are simply deployed relative to the stenosis in the vessel in a suitable position. Then, atherectomy device 90 and cutting portion 92 are deployed relative to guidewire 24 and distal protection device 104 such that cutting portion 92 resides longitudinally adjacent the protective sleeve 108 over guidewire 24. In such an embodiment, cuff 102 need not be provided.

Thus, the present invention provides an atherectomy device which is suitable for debulking the lumen of a vessel to a diameter far greater than the outer diameter of the atherectomy device. This can be accomplished either with or without using cuffs or burrs as in prior art devices, and it is also accomplished by a device which accommodates a standard guidewire or hypotube for guidance.

Although the present invention has been described with reference to preferred embodiments, workers skilled in the art will recognize that changes may be made in form and detail without departing from the spirit and scope of the invention.

What is claimed is:

1. An atherectomy device for removing stenosis from a vessel, comprising:

an elongate drive shaft having a proximal end configured to be coupled to a rotary driver;

a cutting portion extending from a distal end of the drive shaft, the cutting portion including a cutting member having a lumen therethrough and a cutting surface and a preformed shaping member disposed in the lumen, the lumen receiving a guidewire and the preformed shaping member being movable between an insertion shape and a cutting shape, the cutting shape having an overall conformation that is radially larger than that of the insertion shape; and wherein the cutting member is deformable and connected to the shaping member to assume a cutting shape similar to the cutting shape of the shaping member when the shaping member assumes the cutting shape, without changing the outer diameter of the cutting member itself.

2. The atherectomy device of claim 1 wherein the cutting member comprises:

a tubular member defining the lumen and having an inner surface and an outer surface, the outer surface forming the cutting surface.

3. The atherectomy device of claim 2 wherein the drive shaft includes a lumen and wherein the shaping member extends through the lumen in the drive shaft and further comprising:

a protection sleeve positioned radially about the shaping member between the shaping member and an inner lumen wall of the lumen through the drive shaft.

4. The atherectomy device of claim 3 wherein the lumen in the drive shaft and the protection sleeve are configured to receive a guidewire.

5. The atherectomy device of claim 1 wherein the cutting surface comprises an elongate substantially cylindrical surface having an abrasive material attached thereto.

6. The atherectomy device of claim 5 wherein the abrasive material comprises a blade.

7. The atherectomy device of claim 5 wherein the abrasive material comprises a diamond grit.

8. The atherectomy device of claim 1 and further comprising:

an insertion member cooperable with the cutting portion and being configured to selectively maintain the cutting portion in an insertion shape having a lower radial profile than the cutting portion when the cutting member is in the cutting shape.

9. The atherectomy device of claim 8 wherein the insertion member comprises:

a sheath coaxially arranged relative to the cutting portion and longitudinally positionable over the cutting portion to retain the cutting portion in the insertion shape.

10. The atherectomy device of claim 9 wherein the sheath is configured to aspirate stenosis fragments through a distal end thereof.

11. The atherectomy device of claim 1 and further comprising:
a catheter coaxially arranged relative to the drive shaft and configured to aspirate stenosis fragments through a lumen defined therein.

12. The atherectomy device of claim 1 wherein the cutting portion comprises a distal region of the drive shaft.

13. The atherectomy device of claim 1 wherein the shaping member is preformed to form a gentle S-shape in the insertion shape.

14. The atherectomy device of claim 1 wherein the shaping member is preformed to form a helix in the cutting shape.

15. The atherectomy device of claim 1 wherein the shaping member is preformed to form a conical helix in the cutting shape.

16. The atherectomy device of claim 2 wherein the drive shaft includes a lumen in communication with the lumen in the tubular member, the tubular member being configured to aspirate stenotic material therethrough.

17. The atherectomy device of claim 1 wherein the guidewire is advanceable relative to the cutting member, the guidewire including:
a protective sheath disposed thereabout in a region adjacent the cutting member.

18. A method of removing a stenosis from a vessel, comprising:
advancing a substantially linear guidewire through the vessel across the stenosis;
advancing an atherectomy device having a rotary drive shaft and a preshaped cutting portion through the vessel, over the guidewire, to a region proximate the stenosis, the cutting portion having a guidewire lumen therein receiving the guidewire and being selectively movable between an insertion shape and a cutting shape, the cutting shape having a radially enlarged overall conformation relative to the insertion position;
moving the cutting portion from the insertion shape to the cutting shape without changing the outer diameter of the cutting portion itself;
driving the drive shaft to cause rotation of the cutting portion; and
moving the cutting portion across the stenosis.

19. The method of claim 18 wherein moving the cutting portion across the stenosis comprises:
moving the cutting portion across the stenosis from a proximal end thereof to a distal end thereof.

20. The method of claim 18 wherein moving the cutting portion across the stenosis comprises:
moving the cutting portion across the stenosis from a distal end thereof to a proximal end thereof.

21. The method of claim 18 and further comprising, prior to driving the drive shaft:
providing a covering over a portion of the guidewire adjacent the cutting portion to protect the guidewire from the cutting portion.

22. The method of claim 18 wherein moving the cutting portion from the insertion shape to the cutting shape comprises:
retracting a sheath from the cutting portion wherein the sheath, when covering the cutting portion, retains the cutting portion in the insertion shape; and
allowing a preshaped member inside the cutting portion to deform the cutting portion to the cutting shape.

23. The method of claim 18 wherein the cutting portion and the drive shaft form a lumen therethrough and further comprising:
aspirating embolic material through a distal end of the cutting portion and through the lumen defined by the drive shaft and cutting portion.

24. The method of claim 18 and further comprising:
aspirating emboli from a region proximate a distal end of the cutting portion.

25. An atherectomy device for cutting a restriction in a blood vessel, comprising:
an elongate cutting member having a lumen therein, the lumen being sized to track over a guidewire;
a drive shaft coupled to the cutting member to drive rotation of the cutting member;
an elongate shaping member cooperable with the cutting member and disposed generally longitudinally relative to the cutting member, the shaping member having an insertion conformation and an expanded conformation, the expanded conformation being radially expanded relative to the insertion conformation, the shaping member being configured to deform the cutting member from an insertion shape into a cutting shape as the shaping member moves from the insertion conformation to the expanded conformation without changing an outer diameter of the cutting member itself; and
an insertion device cooperable with the cutting member and configured to selectively retain the cutting member in the insertion shape.

26. The atherectomy device of claim 25 wherein the insertion device comprises:
a sheath longitudinally slidable over the cutting member to retain the cutting member in the insertion shape.

27. An atherectomy device for removing stenosis from a vessel, comprising:
an elongate drive shaft having a lumen, and a proximal end configured to be coupled to a rotary driver;
a cutting portion extending from a distal end of the drive shaft, the cutting portion including a tubular cutting member, receiving a guidewire and having an outer cutting surface, and a preformed shaping member disposed in the lumen of the drive shaft and the lumen of the tubular member, the preformed shaping member being movable between an insertion shape and a cutting shape, the cutting shape having an overall conformation that is radially larger than that of the insertion shape;
wherein the cutting member is deformable and connected to the shaping member to assume a cutting shape similar to the cutting shape of the shaping member when the shaping member assumes the cutting shape, without changing the outer diameter of the cutting member itself; and
a protection sleeve positioned radially about the shaping member between the shaping member and an inner lumen wall of the lumen through the drive shaft.

28. An atherectomy device for removing stenosis from a lumen, comprising:
an elongate drive shaft having a proximal end configured to be coupled to a rotary driver;
a cutting portion extending from a distal end of the drive shaft, the cutting portion including a cutting member having an elongate tubular cutting surface having a blade attached thereto and a preformed shaping member cooperable therewith, the preformed shaping member being movable between an insertion shape and a cutting shape, the cutting shape having an overall conformation that is radially larger than that of the insertion shape; and wherein the cutting member is deformable and connected to the shaping member to assume a cutting shape similar to the cutting shape of the shaping member when the shaping member assumes the cutting shape, without changing the outer diameter of the cutting member itself.

29. An atherectomy device for removing stenosis from a lumen, comprising:

an elongate drive shaft having a proximal end configured to be coupled to a rotary driver;

a cutting portion extending from a distal end of the drive shaft, the cutting portion and connected to a guidewire including a cutting member having a cutting surface, and a preformed shaping member cooperable therewith, the preformed shaping member being movable between an insertion shape and a cutting shape, the cutting shape having an overall conformation that is performed to form a helix and is radially larger than that of the insertion shape; and wherein the cutting member is deformable and connected to the shaping member to assume a cutting shape similar to the cutting shape of the shaping member when the shaping member assumes the cutting shape, without changing the outer diameter of the cutting member itself.

30. An atherectomy device for removing stenosis from a lumen, comprising:

an elongate drive shaft having a proximal end configured to be coupled to a rotary driver;

a cutting portion extending from a distal end of the drive shaft, the cutting portion including a cutting member having a cutting surface and a preformed shaping member cooperable therewith, the preformed shaping member being movable between an insertion shape and a cutting shape, the cutting shape having an overall conformation that is performed to form a conical helix and is radially larger than that of the insertion shape; and wherein the cutting member is deformable and connected to the shaping member to assume a cutting shape similar to the cutting shape of the shaping member when the shaping member assumes the cutting shape, without changing the outer diameter of the cutting member itself.

\* \* \* \* \*

UNITED STATES PATENT AND TRADEMARK OFFICE
CERTIFICATE OF CORRECTION

PATENT NO. : 5,843,103
DATED : December 1, 1998
INVENTOR(S) : E.I Wulfman

It is certified that error appears in the above-identified patent and that said Letters Patent is hereby corrected as shown below:

| COLUMN | LINE | |
|---|---|---|
| 13 | 12 | "shaft, the cutting portion and connected to a guidewire" should read --shaft and connected to a guidewire, the cutting portion-- |

Signed and Sealed this

Fourteenth Day of December, 1999

Attest:

Q. TODD DICKINSON

*Attesting Officer*   Acting Commissioner of Patents and Trademarks